US006607712B2

(12) United States Patent
Majeed et al.

(10) Patent No.: US 6,607,712 B2
(45) Date of Patent: Aug. 19, 2003

(54) COMPOSITION AND METHODS CONTAINING AN ANTIMICROBIAL ESSENTIAL OIL EXTENDED FROM COLEUS FORSKOHLII

(75) Inventors: Muhammed Majeed, Piscataway, NJ (US); Subbalakshmi Prakash, Piscataway, NJ (US)

(73) Assignee: Sabinsa Corporation, Piscataway, NJ (US)

( * ) Notice: Subject to any disclaimer, the term of this patent is extended or adjusted under 35 U.S.C. 154(b) by 0 days.

(21) Appl. No.: 10/078,262

(22) Filed: Feb. 20, 2002

(65) Prior Publication Data

US 2002/0160066 A1 Oct. 31, 2002

Related U.S. Application Data

(60) Provisional application No. 60/269,330, filed on Feb. 20, 2001.

(51) Int. Cl.⁷ .......................... A61K 35/78; A61K 7/06; A61K 31/74; A61K 7/26
(52) U.S. Cl. .......................... 424/58; 514/455; 514/510; 424/74; 424/78.03; 424/725; 424/773
(58) Field of Search ................ 424/78.03, 725, 424/58, 74, 773; 514/455, 510

(56) References Cited

U.S. PATENT DOCUMENTS 5,804,596 A * 9/1998 Majeed et al. .............. 514/455
6,248,309 B1 * 6/2001 Iyer et al. .................... 424/49

OTHER PUBLICATIONS

Computer CABA Abstract 2002:59346 Demo et al Higiene Alimentar (2001) vol. 15 No. 85 pp. 87–90.*
Computer DWPI Abstract 2002–247345 JP2001348308 Published Mar. 13, 2000.*

* cited by examiner

*Primary Examiner*—Herbert J. Lilling
(74) *Attorney, Agent, or Firm*—Arent Fox Kintner Plotkin & Kahn, PLLC

(57) ABSTRACT

An essential oil composition from *Coleus forskohlii* is used in compositions and methods for the treatment of skin infections and in the prevention and treatment of dental caries.

48 Claims, 8 Drawing Sheets

Bornyl acetate 3-decanone alpha-pinene beta-pinene alpha-humulene (-)-alpha-gurjunene alpha-selinene Growth inhibition of *Streptococcus mutans* by the essential oil composition

ANTIFUNGAL ACTIVITY OF *COLEUS FORSKOHLII* OIL

INHIBITORY EFFECTS OF *COLEUS FORSKOHLII* OIL ON THE GROWTH OF CANDIDA ALBICANS (ATCC 11006) AS COMPARED TO THE ANTIFUNGAL AGENT NYSTATIN

ANTIBACTERIAL ACTIVITY OF *COLEUS FORSKOHLII* OIL AGAINST *STREPTOCOCCUS EPIDERMIDIS (ATCC 14990)*

INHIBITORY EFFECTS OF COLEUS FORSKOHLII OIL AGAINST THE GROWTH OF *STREPTOCOCCUS EPIDERMIDIS* (ATCC 14990), AS COMPARED TO CHLORAMPHENICOL (30 mcg)

COMPARATIVE INHIBITORY EFFECTS OF COLEUS FORSKOHLII ESSENTIAL OIL AND CHLORAMPHENICOL AGAINST *STAPHYLOCOCCUS AUREUS* (ATCC 29213)

COMPARATIVE EFFICACY OF COLEUS FORSKOHLII ESSENTIAL OIL AND CHLORAMPHENICOL AGAINST *E. COLI*.

COMPOSITION AND METHODS CONTAINING AN ANTIMICROBIAL ESSENTIAL OIL EXTENDED FROM *COLEUS FORSKOHLII*

This application claims the benefit of U.S. Provisional Application No. 60/269,330 filed Feb. 20, 2001.

FIELD OF THE INVENTION

The present invention is related to an essential oil composition derived from *Coleus forskohlii* and more particularly to compositions and methods of preparing and utilizing the composition to treat microbial infections.

BACKGROUND OF THE INVENTION

*Coleus forskohlii* belongs to the Natural Order Labiatae (Lamiaceae), a family of mints and lavenders. This species is a perennial herb with fleshy, fibrous roots that grows wild in the warm sub-tropical temperate areas in India, Burma and Thailand. In India, it is cultivated for use as a condiment (Bruneton, 1995). In recent years the plant has gained pharmacological importance as the only known plant source of the adenylate cyclase activating compound, forskolin (de Souza, 1991). Forskolin-rich extracts are commercially obtained from the roots. The roots also yield a viscous, dark brown colored essential oil containing a range of aroma constituents that collectively impart a pleasing delicate aroma with a spicy note (Misra, et. al., 1994). The oil can be obtained as a valuable by-product of forskolin-rich extract production, without detrimental effects on the yield of forskolin.

Over forty compounds belonging to four classes of aroma compounds have been recovered from oils obtained from various indigenous genotypes of the plant (Misra, et al., 1994). These include sesquiterpenes, sesquiterpene alcohols, monoterpenoids and diterpenoids.

SUMMARY OF THE INVENTION

From research on the bioactive constituents of essential oils, it has been found that a number of terpenoid constituents have antimicrobial properties. In the embodiments of the present invention, a novel composition of and methods of preparing and utilizing an essential oil from *Coleus forskohlii*, providing antimicrobial action is achieved.

DETAILED DESCRIPTION OF THE PREFERRED EMBODIMENTS

Figure 1:
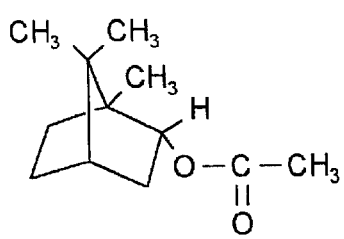
FIG. 1 shows the structures of principal chemical constituents of a composition in accordance with an embodiment of this invention.
Figure 1:
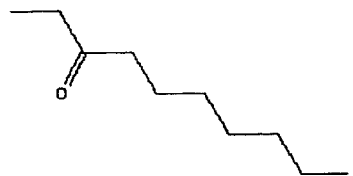
Figure 1:
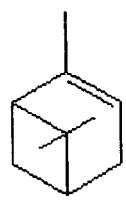
Figure 1:
Figure 1:
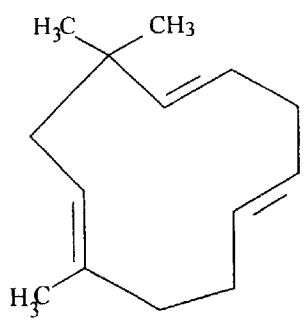
Figure 1:
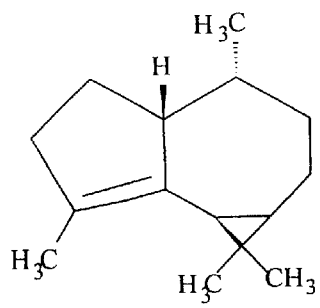
Figure 1:
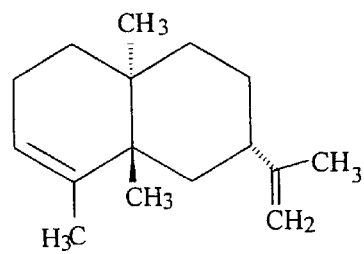

In embodiments of the present invention, an essential oil composition from the plant *Coleus forskohlii* can be extracted and utilized in compositions and methods for the treatment of microbial infections.

EXAMPLE

A first exemplary embodiment of a method for extracting embodiments of a novel composition in accordance with this invention is described below.

Materials and Methods

Plant Material

*Coleus forskohlii* root powder was obtained from Sabinsa Corporation of Piscataway, N.J. and was imported from India.

Extraction and purification of the essential oil. A supercritical extraction process with carbon dioxide was employed. A batch extraction device was used, wherein the material was extracted with liquid carbon dioxide. 80 kg of the powdered root material were charged into the carbon dioxide extraction chamber and contacted with carbon dioxide for 2 hours. Each 80 kg charge yielded 10 kg of an enriched material containing the essential oil. The crude essential oil was purified by solvent extraction, the impurities were crystallized out and the dissolved oil fraction was decolorized, followed by solvent removal by distillation. The light brown colored essential oil obtained was further purified by distillation through a packed column at 70° C. and 5–6 mm pressure to yield a light yellow colored oil (specific gravity 0.865) with a characteristic odor.

GC-MS Analysis. The purified oil was analyzed on a Hewlett-Packard GCD system with Innowax FSC column, using Helium as the carrier gas. The injector temperature was 250° C. and the split flow rate was 1 ml/min. The GC oven temperature was maintained at 60° C. for 10 minutes and programmed to 220° C. at the rate of 40° C./min, then kept constant at 220° C. for 10 minutes followed by increase to 240° C. at the rate of 10° C./min. MS data were obtained at 70 eV and a mass range of 45–400. The relative percentage levels of the major constituents were calculated from the TIC.

Determination of the antimicrobial activity of the composition. The sensitivity of *Propionbacterium acnes* a microorganism associated with acne and other skin infections (Nishijima, et al. (2000)), *Staphylococcus aureus* a bacterial strain found in infected wounds and skin eruptions including acne (Nishijima, et al. 1994)), *Staphylococcus epidermidis* a bacterial strain occurring in a variety of opportunistic bacterial skin infections and in acne (Nishijima, S. et al. (2000)) and *Streptococcus mutans*, a bacterial strain associated with the progression of dental caries (Sanchez-Perez, L. et al. (2001)), *Candida albican*, and *Streptococcus epidermidis*; to *Coleus forskohlii* oil using disk diffusion methodology was determined. One strain each of *Propionbacterium acnes* (ATCC 11827), *Staphylococcus aureus* (ATCC 29213), *Streptococcus mutans* (ATCC 25175), and *Staphylococcus epidermidis* (ATCC 14990) *Candida albicans* (ATCC 11006) and *Streptococcus epidermidis* (ATCC 14990) were obtained from ATCC. *Propionbacterium acnes* culture were grown in Reinforced Clostridia media under anaerobic conditions at 37° C. for 24 hours. *Staphylococcus aureus, Streptococcus mutans* and *Staphylococcus epidermidis* cultures were cultured in Trypticase Soy Broth under aerobic conditions at 37° C. for 24 hours. The essential oil was diluted in both autoclaved mineral oil and ethanol to yield concentrations of essential oil ranging from 0 to 100%. Sensitivity of the bacterial strains to the oil was tested on TSA-Blood Agar plates (Laboratory Media Incorporated). Plates were inoculated with 200 μl of a 0.5 to 1.0 MacFarland (about 5×10$^7$ cells). This suspension was obtained by resuspending the pellet obtained from 1.5 ml of culture (10,000× g, 3 minutes) in 0.45% saline buffer (for the aerobes) or anaerobe diluent (for *P. acnes*). Anaerobe diluent was purchased from Anaerobe Systems. The plate was dried for about 30 minutes prior to application of the disks. All procedures involving *P. acnes* were performed in an anaerobe chamber. The antimicrobial properties of the essential oil composition were tested after dilution of the test oil in mineral oil. This was accomplished by placing one to two dilution disks (12.7 mm) on the inoculated plate. Forty microliters of the diluted test oil was applied to the disk. Additionally, dilutions of the essential oil in ethanol were tested against *P. aches*. For this test, forty microliters of each essential oil/ethanol dilution was placed on each disk prior to application to the inoculated plates. The disks were allowed to dry for at least 30 minutes. One to two disks (embedded with the test oil) were placed on each plates. Each concentration of the test compound was tested in duplicate for both the ethanol and mineral oil dilution procedures. Plates inoculated with *Propionhacterium acnes* were incubated under anaerobic conditions at 37° C. for 48 hours. Plates inoculated with *Staphylococcus aureus* and epidermidis were incubated under aerobic conditions at 37° C. for 24 hours. Plates inoculated with *Streptococcus mutans* were incubated under aerobic conditions at 37° C. for 5 days. Inhibition zones were measured to the closest one tenth of one millimeter using a caliper.

Results and Discussion

GC-MS was used to identify constituents of the essential oil (FIG. 1). The principal constituents identified were bornyl acetate ($C_{12}H_{20}O_2$, Molecular weight 196, CAS #5655-61-8, 15.0%), 3-decanone ($C_{10}H_{20}O$, Molecular weight 156, CAS #928-80-3, 7.0%), an azulene derivative (sesquiterpene) ($C_{15}H_{24}$, Molecular weight 204, CAS #3691-11-0, 7.5%), alpha-pinene ($C_{10}H_{16}$, Molecular weight 136, CAS #80-56-8, 2.0%) and beta-pinene ($C_{10}H_{16}$, Molecular weight 136, CAS #18172-67-3, 1.5%). Other identified components include alpha-humulene ($C_{15}H_{24}$, Molecular weight 204.36), alpha-gurjunene ($C_{15}H_{24}$, Molecular weight 204.36) and alpha-selinene ($C_{16}H_{26}$, Molecular weight 218.39)

*Coleus forskojlii* oil was found to inhibit *Candida albicans* (ATCC 11006) effectively at concentrations ranging from 7.5 to 30 mcg. The zones of inhibition produced were larger than those produced by the antifungal agent Nystatin (20 mcg per disc).

*Coleus forskojlii* oil was found to produce zones of inhibition which were larger than those produced with Chloramphenicol (30 mcg) at 30 mcg concentration, suggesting its superior in vitro antibacterial effects against *S. epidermidis* (ATCC 194990) at 30 mcg concentration.

Figure 2:
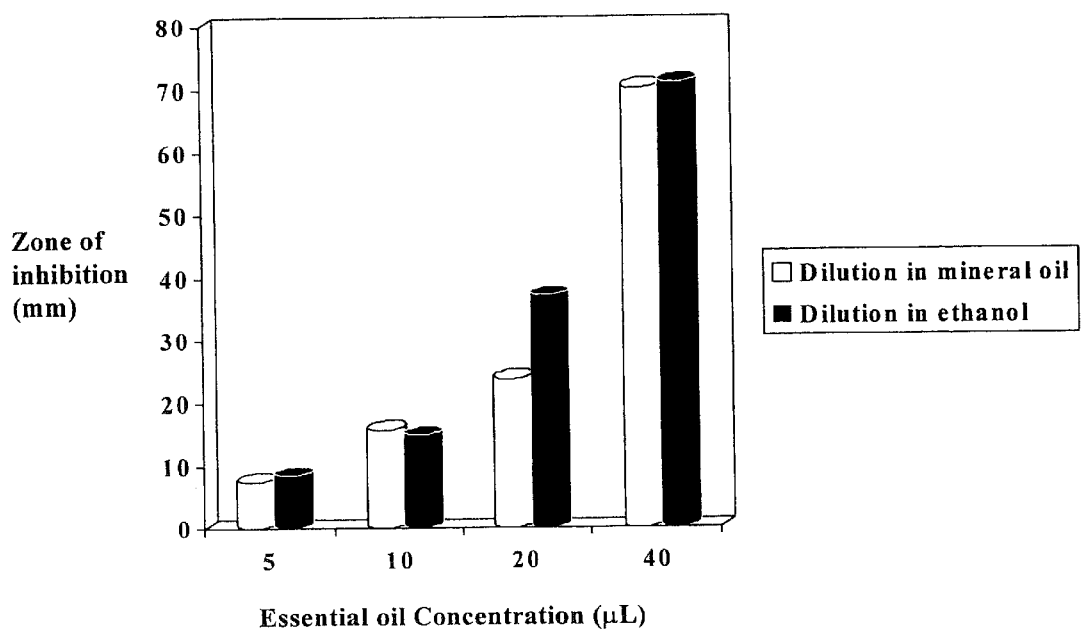
FIG. 2 shows the growth inhibition of *Propionibacterium acnes* by the essential oil composition of FIG. 1 in accordance with an embodiment of this invention.

*Coleus forskojlii* oil showed significant antimicrobial activity against *P. acnes* (ATCC 11827), when present in amounts of 10, 20 and 40 μL per disk. (FIG. 2)

Figure 3:
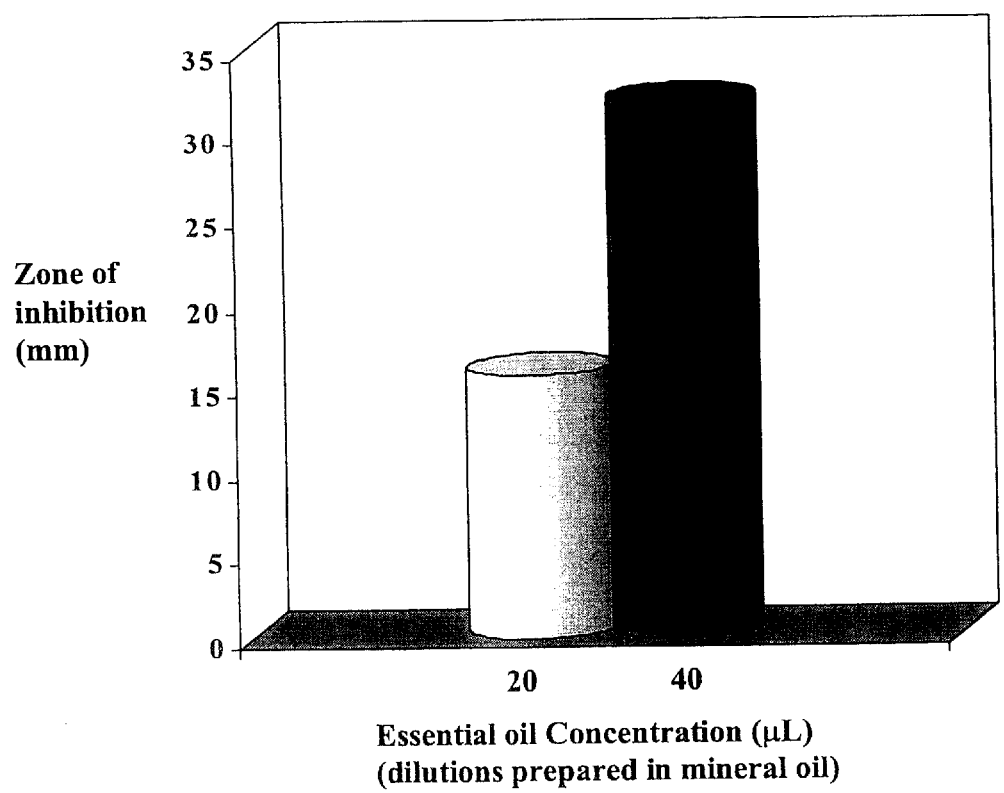
FIG. 3 shows the growth inhibition of *Staphylococcus aureus* by the essential oil composition of FIG. 1 in accordance with an embodiment of this invention.
Figure 4:
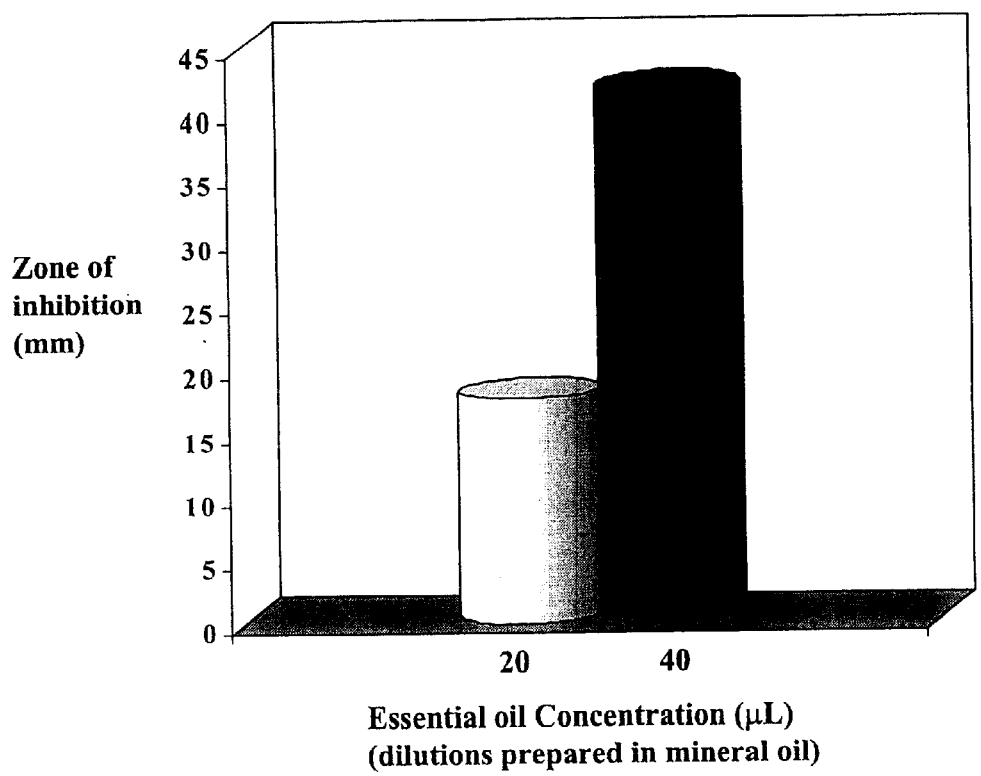
FIG. 4 shows the growth inhibition of *Staphylococcus epidermidis* by the essential oil composition of FIG. 1 in accordance with an embodiment of this invention.
Figure 5:
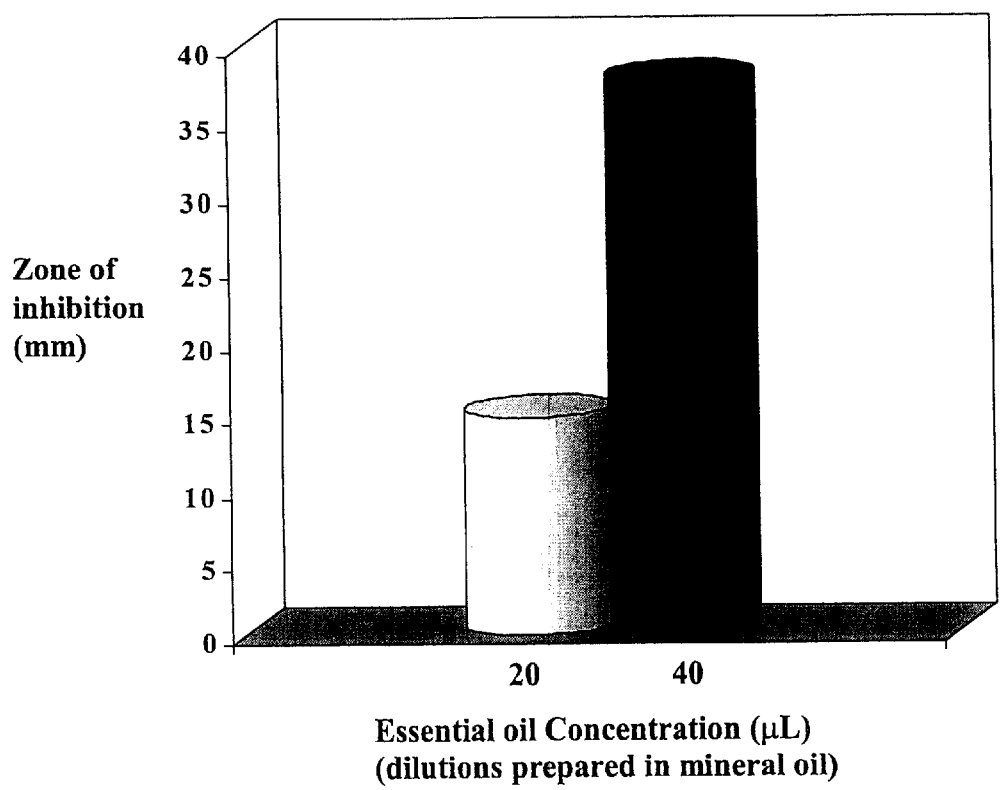
FIG. 5 shows the growth inhibition of *Streptococcus mutans* by the essential oil composition of FIG. 1 in accordance with an embodiment of this invention.
Figure 6:
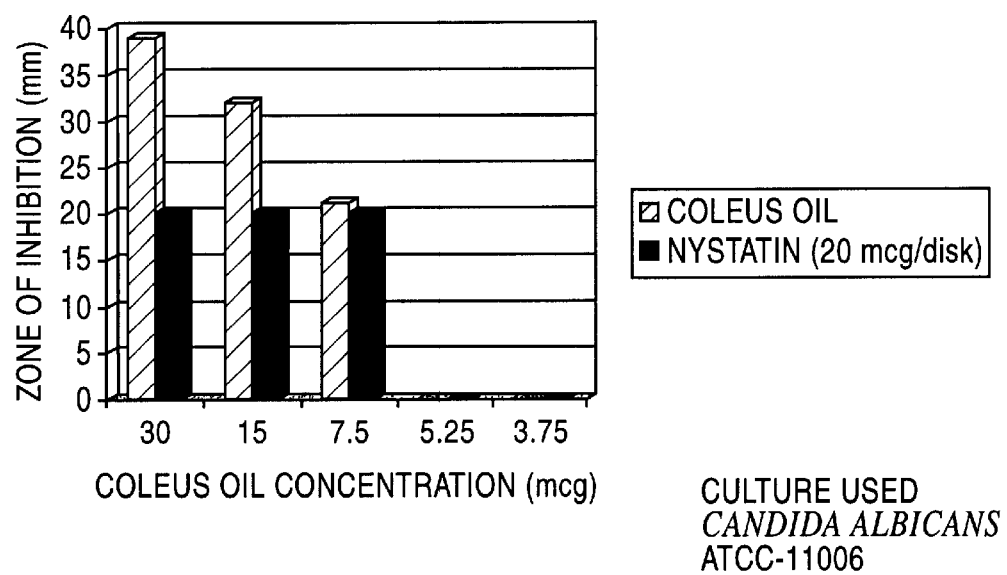
FIG. 6 shows the growth inhibition of *Candida albicans* by the essential oil composition of FIG. 1 in accordance with an embodiment of this invention, as compared to the antifungal agent Nystatin.
Figure 7:
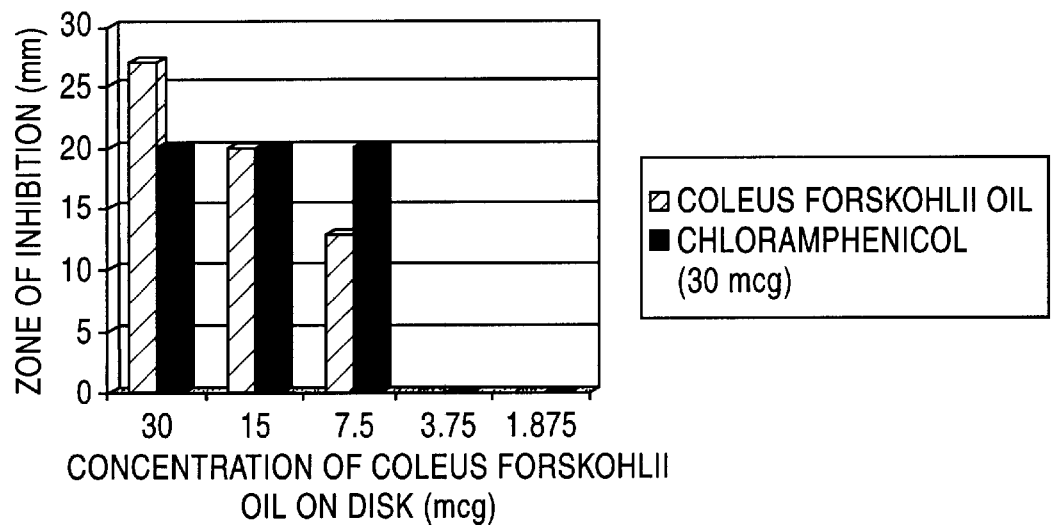
FIG. 7 shows the growth inhibition of *Streptococcus epideridis* by the essential oil composition of FIG. 1 in accordance with an embodiment of this invention, as compared to Chloramphenicol.

For *S. aureus* (ATCC 29213) (FIG. 3), *S. epidermidis* (ATCC 14990) (FIG. 4) and *S. mutans* (ATCC 25175) (FIG. 5) significant zones of inhibition were observed with 20 and 40 μL of essential oil per disk, with the dilutions prepared in mineral oil.

In a second exemplary study, cultures chosen for the study included *Staphylococcus aureus* and *E. coli*. As a comparison, an antibiotic (Chloramphenicol 30 μg/disk) was also kept as a reference. The results are given in the table below.

| Bacteria tested | Amount of test compound on the disk (μl) | | | | | Chloramphenicol 30 μg |
|---|---|---|---|---|---|---|
| | 1.875 | 3.75 | 7.5 | 15.0 | 30.0 | |
| *Staphylococcus aureus* | 6 | 6.5 | 8 | 18 | 29.5 | 20 |
| *E.coli* | 7 | 8 | 8 | 9 | 12 | 34 |

The values indicated are clearance of zone in mm.

Figure 8:
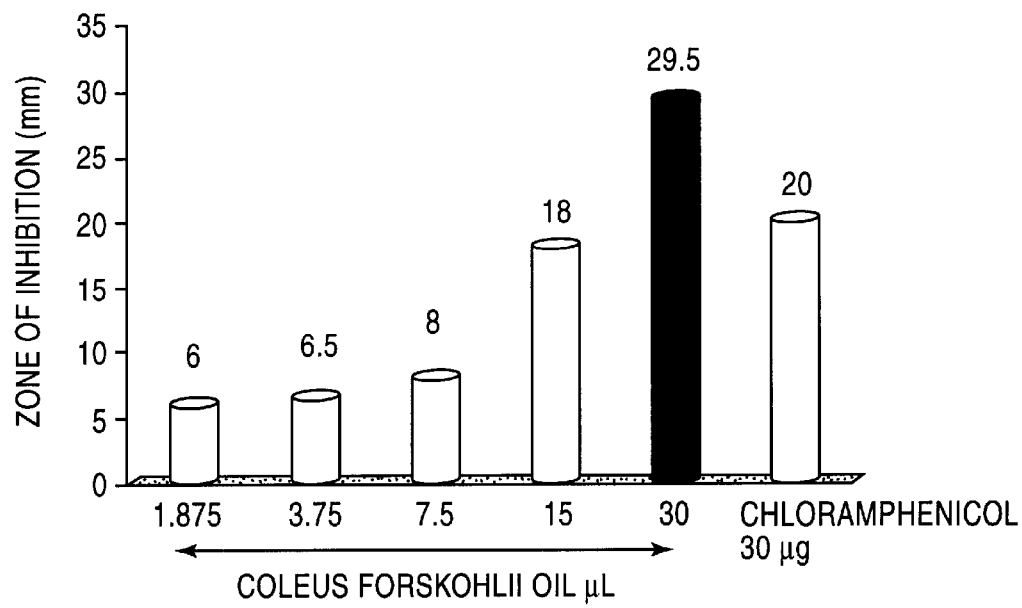
FIG. 8 shows the growth inhibition of *Staphylococcus aureus* (ATCC 29213) by the essential oil composition of FIG. 1 in accordance with an embodiment of this invention, as compared to Chloramphenicol.

As shown in FIG. 8, at 30 μL concentration, *Coleus forskohlii* oil had greater inhibitory activity than 30 μg of chloramphenicol under similar experimental conditions.

Figure 9:
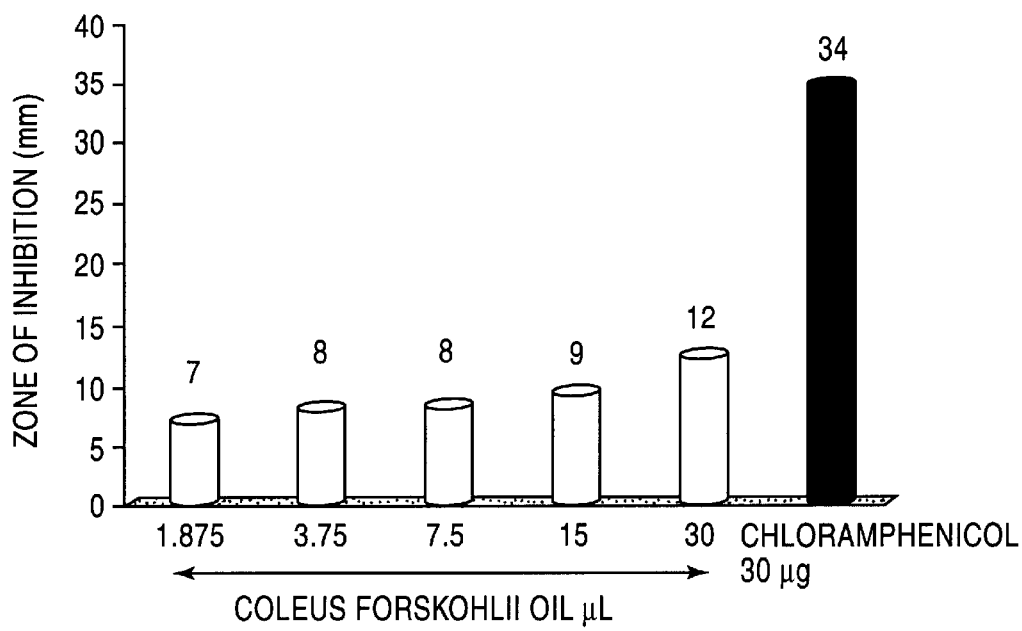
FIG. 9 shows the growth inhibition of *E. coli* by the essential oil composition of FIG. 1 in accordance with embodiments of this invention, as compared to Chloramphenicol.

As FIG. 9 shows, *Coleus forskohlii* essential oil showed inhibitory activity against *E. coli*, although this was not as significant as Chloramphenicol under similar experimental conditions.

Dermal Irritation Studies

Primary skin irritation test on rabbits with *Coleus forskohlii* oil and the results are summarized below.

The study was designed to determine the primary skin irritation potential of the test substance. The test substance in the amount of 0.5 ml was applied to shorn back skin both intact and abraded site of three rabbits per sex. Each site of application was carefully observed and the reaction evaluated according to Draize's method at 24 and 72 hours.

No erythema or edema of skin was observed at abraded and intact site after application of test substance.

The compound did not cause irritation to skin in rabbits.

Primary skin irritation score =0.00

In summary, the essential oil composition from *Coleus forskohlii* shows significant inhibitory action against *P. acnes* (ATCC 11827), *S. aureus* (ATCC 29213), *S. epidermidis* (ATCC 14990) *S. mutans* (ATCC 25175), *Candida albicans* (ATCC 11006) *S. epidermidis* (ATCC 194990) and *E. coli*. The composition therefore represents a novel natural essential oil for use in, for example, skin care formulations for the treatment of skin infections such as acne and oral care formulations for the prevention and treatment of dental caries.

*Coleus forskohlii* oil also represents a novel essential oil for use in oral and topical preparations for candidal infections.

In the embodiments of this invention, the essential oil contains at least 7.5% bornyl acetate, at least 3.5%

3-decanone, at least 3.75% of an azulene derivative, at least 1% alpha-pinene and at least 0.75% beta-pinene. Preferably, the essential oil composition contains at least 15% bornyl acetate, at least 7% 3-decanone, at least 7.5% sesquiterpene, at least 2% alpha-pinene and at least 1.5% beta-pinene. Most preferably, the essential oil composition contains about 15% bornyl acetate, 7% 3-decanone, 7.5% sesquiterpene, 2% alpha-pinene and 1.5% beta-pinene.

In some embodiments of this invention, the essential oil composition may be applied in a cream or ointment or, particularly for oral/peridontal treatments, as a paste. Generally, creams, ointments or pastes will contain an effective amount of the essential oil composition. In these embodiments, the cream, ointment or paste should contain at least 0.5% of the essential oil composition. Broadly, the cream, ointment or paste may contain 0.5% to 25% or more of the essential oil composition. In some embodiments the cream, ointment or paste may contain 0.5, 1, 2 or 5% to 10, 15 or 20% of the essential oil composition.

The following is a list of literature cited in this application, each of which is hereby incorporated by reference in its entirety:

LITERATURE CITED

Bruneton, Jean. *Coleus forskohlii*. in Pharmacognosy, Phytochemistry, Medicinal Plants, Lavoisier publishing Company, 1995, 521.

de Souza, N. J. *Coleus forskohlii* Briq.—The Indian plant source for forskolin. Recent Advances in Medicinal, Aromatic & Spice crops, (ed: S. P. Raychaudhuri.) Today and Tomorrow's printers and Publishers, New Delhi, India, 1991, Vol I: 83–91.

Misra, L. N; Tyagi, B. R.; Ahmad, A. and Bahl, J. B. Variability of the chemical composition of the essential oil of *Coleus forskohlii* genotypes. J. Essential Oil Res. 1994, 6, 243–247.

Nishijima, S., Kurokawa, I., Katoh, N. and Watanabe, K. The bacteriology of acne vulgaris and antimicrobial susceptibility of *Propionibacterium acnes* and *Staphylococcus epidermidis*. J. Dermatol. 2000, 27,318–323.

Nishijima, S.; Namura, S.; Kawai, S.; Akamatsu, H.; Asada, Y.; and Kawabata, S. Sensitivity of *Staphylococcus aureus* and *Streptococcus pyogenes* isolated from skin infections in 1992 to antimicrobial agents, J. Dermatol. 1994, 21, 233–238.

Sanchez-Perez, L. and Enrique Acosta-Gio A. Caries risk assessment from dental plaque and salivary *Streptococcus mutans* counts on two culture media. Arch. Oral Biol. 2001, 46, 49–55.

What is claimed is:

1. A method of inhibiting microbial growth comprising contacting at least one microbe selected from the group consisting of *Propionibacterium acnes, Staphylococcus aureus, Staphylococcus epidermidis, Streptococcus mutans, Candida albicans, Escherichia coli, Steptococcus epidermidis* and mixtures thereof with an essential oil composition isolated from *Coleus forskohlii*, wherein the essential oil composition comprises bornyl acetate, 3-decanone, an azulene derivative, aipha-pinene and beta-pinene.

2. The method of claim 1, wherein the essential oil composition comprises at least 7.5% bornyl acetate, at least 3.5% 3-decanone, at least 3.75% of an azulene derivative, at least 1% alpha-pinene and at least 0.75% beta-pinene.

3. The method of claim 1 wherein the essential oil composition is isolated by extracting an essential oil from *Coleus forskohlii* root material with carbon dioxide and a solvent or solvents.

4. The method of claim 2, wherein the growth of *Propionibacterium acnes* is inhibited.

5. The method of claim 2, wherein the growth of *Staphylococcus aureus* is inhibited.

6. The method of claim 2, wherein the growth of *Staphylococcus epidermidis* is inhibited.

7. The method of claim 2, wherein the growth of *Streptococcus mutans* is inhibited.

8. The method of claim 2, wherein the growth of *Candida albicans* is inhibited.

9. The method of claim 2, wherein the growth of *Steptococcus epidermidis* is inhibited.

10. The method of claim 3, wherein the growth of *E. coli* is inhibited.

11. A method of inhibiting microbial growth comprising contacting microorganisms with an essential oil composition isolated from *Coleus forskohlii*, wherein the essential oil composition comprises bornyl acetate, 3-decanone, an azulene derivative, alpha-pinene and beta-pinene.

12. The method of claim 11, wherein the essential oil composition comprises at least 7.5% bornyl acetate, at least 3.5% 3-decanone, at least 3.75% of an azulene derivative, at least 1% alpha-pinene and at least 0.75% beta-pinene.

13. The method of claim 12, wherein the essential oil composition comprises at least 15% bornyl acetate, at least 7% 3-decanone, at least 7.5% sesquiterpene, at least 2% alpha-pinene and at least 1.5% beta-pinene.

14. The method of claim 13, wherein the essential oil composition comprises about 15% bornyl acetate, 7% 3-decanone, 7.5% sesquiterpene, 2% alpha-pinene and 1.5% beta-pinene.

15. The method of claim 12, wherein the microorganisms are *Propionibacterium acnes*.

16. The method of claim 12, wherein the microorganisms are *Staphylococcus aureus*.

17. The method of claim 12, wherein the microorganisms are *Staphylococcus epidermidis*.

18. The method of claim 12, wherein the microorganisms are *Streptococcus mutans*.

19. The method of claim 12, wherein the microorganisms are *Candida albicans*.

20. The method of claim 12, wherein the microorganisms are *Steptococcus epidermidis*.

21. The method of claim 12, wherein the microorganisms are *E. coli*.

22. The method of claim 11, wherein the essential oil composition is isolated by extracting a *Coleus forskohlii* root material with carbon dioxide and a solvent or solvents.

23. The method of claim 11, wherein the essential oil composition comprises at least 15% bornyl acetate, at least 7% 3-decanone, at least 7.5% sesquiterpene, at least 2% alpha-pinene and at least 1.5% beta-pinene.

24. The method of claim 11, wherein the essential oil composition comprises about 15% bornyl acetate, 7% 3-decanone, 7.5% sesquiterpene, 2% alpha-pinene and 1.5% beta-pinene.

25. The method of claim 1 wherein the essential oil composition is administered topically to the skin of a patient.

26. The method of claim 3 wherein the essential oil composition has been isolated by the steps of a) extracting an essential oil from *Coleus forskohlii* root material by supercritical extraction with carbon dioxide; then b) purifying of the extracted essential oil from step (a) by solvent extraction; then c) removing impurities from the essential oil from step (b) by crystallization; and then d) further purifying of the essential oil from step (c) by distillation.

27. The method of claim 3, wherein the growth of *Propionibacterium acne* is inhibited.

28. The method of inhibiting growth of claim 3, wherein the growth of *Staphylococcus aureus* is inhibited.

29. The method of inhibiting growth of claim 3, wherein the growth of *Staphylococcus epidermidis* is inhibited.

30. The method of inhibiting growth of claim 3, wherein the growth of *Streptococcus mutans* individuals is inhibited.

31. The method of inhibiting growth of claim 3, wherein the growth of *candida albicans* is inhibited.

32. The method of inhibiting growth of claim 3, wherein the growth of *Steptococcus epidermidis* is inhibited.

33. The method of inhibiting growth of claim 3, wherein the growth of *E. coli* is inhibited.

34. A method of treating a patient having a microbial infection and in need of such a treatment, comprising administering an anti-microbial amount of an essential oil composition isolated from *Coleus forskohlii* in the patient, wherein the essential oil composition comprises bornyl acetate, 3-decanone, an azulene derivative, alpha-pinene and beta-pinene.

35. The method of claim 34, the patient having a microbial peridontal infection, wherein the essential oil composition is administered topically to at least a portion of the mouth of the patient.

36. The method of claim 34, the patient having a microbial skin infection, wherein the essential oil composition is administered topically to at least a portion of the skin of the patient.

37. The method of claim 34, wherein the essential oil composition is isolated by extracting a *Coleus forskohlii* root material with carbon dioxide and a solvent or solvents.

38. The method of claim 34, wherein the essential oil composition comprises at least 7.5% bornyl acetate, at least 3.5% 3-decanone, at least 3.75% of an azulene derivative, at least 1% alpha-pinene and at least 0.75% beta-pinene.

39. The method of claim 38, wherein the essential oil composition comprises at least 15% bornyl acetate, at least 7% 3-decanone, at least 7.5% sesquiterpene, at least 2% alpha-pinene and at least 1.5% beta-pinene.

40. The method of claim 39, wherein the essential oil composition comprises about 15% bornyl acetate, 7% 3-decanone, 7.5% sesquiterpene, 2% alpha-pinene and 1.5% beta-pinene.

41. The method of claim 36, wherein the essential oil composition is isolated by extracting a *Coleus forskohlii* root material with carbon dioxide and a solvent or solvents.

42. The method of claim 36, wherein the essential oil composition comprises at least 7.5% bornyl acetate, at least 3.5% 3-decanone, at least 3.75% of an azulene derivative, at least 1% alpha-pinene and at least 0.75% beta-pinene.

43. The method of claim 42, wherein the essential oil composition comprises at least 15% bornyl acetate, at least 7% 3-decanone, at least 7.5% sesquiterpene, at least 2% alpha-pinene and at least 1.5% beta-pinene.

44. The method of claim 43, wherein the essential oil composition comprises about 15% bornyl acetate, 7% 3-decanone, 7.5% sesquiterpene, 2% alpha-pinene and 1.5% beta-pinene.

45. The method of claim 35, wherein the essential oil composition is isolated by extracting a *Coleus forskohlii* root material with carbon dioxide and a solvent or solvents.

46. The method of claim 35, wherein the essential oil composition comprises at least 7.5% bornyl acetate, at least 3.5% 3-decanone, at least 3.75% of an azulene derivative, at least 1% alpha-pinene and at least 0.75% beta-pinene.

47. The method of claim 46, wherein the essential oil composition comprises at least 15% bornyl acetate, at least 7% 3-decanone, at least 7.5% sesquiterpene, at least 2% alpha-pinene and at least 1.5% beta-pinene.

48. The method of claim 47, wherein the essential oil composition comprises about 15% bornyl acetate, 7% 3-decanone, 7.5% sesquiterpene, 2% alpha-pinene and 1.5% beta-pinene.

* * * * *